United States Patent [19]
Balz et al.

[11] Patent Number: 5,132,295
[45] Date of Patent: Jul. 21, 1992

[54] ALGINATE-BASED VERAPAMIL-CONTAINING DEPOT DRUG FORM

[75] Inventors: Evamarie Balz, Weinheim; Heinz Einig, Neustadt; Peter Dresen, Viernheim, all of Fed. Rep. of Germany

[73] Assignee: Knoll AG, Ludwigshafen, Fed. Rep. of Germany

[21] Appl. No.: 640,408

[22] Filed: Jan. 24, 1991

[30] Foreign Application Priority Data

Jul. 13, 1988 [DE] Fed. Rep. of Germany ....... 3823693

[51] Int. Cl.$^5$ ................ A61K 9/30; A61K 31/275; A61K 9/22; A61K 9/26
[52] U.S. Cl. ................ 514/54; 424/464; 424/468; 424/469; 424/474; 424/475; 536/3; 514/254; 514/523; 514/779; 514/964; 514/965
[58] Field of Search ........... 514/54, 964, 965, 254, 514/523, 779; 536/3; 424/464, 468, 469, 474, 475

[56] References Cited

FOREIGN PATENT DOCUMENTS 0063266 10/1982 European Pat. Off. .
2207353 1/1989 United Kingdom .

OTHER PUBLICATIONS

Arzneim.-Forsch (Drig Res.) vol. 25, No. 8, Aug. 1975, D. Mayer et al.: "Entwicklung einer oralen Retard-form von Verapamil und Prufung der Resorption am narkotisierten Hund", pp. 1272–1275.

Journal of Controlled Release, vol. 3, No. 2-3, Mar. 1986, Elsevier Science Publishers B.V. (Amsterdam, NL), A. F. Stockwell et al.: "In Vitro Evaluation of Alginate Gel Systems as Sustained Release Drug Delivery Systems", pp. 167–175.

*Primary Examiner*—Ronald W. Griffin
*Attorney, Agent, or Firm*—Oblon, Spivak, McClelland, Maier & Neustadt

[57] ABSTRACT

An alginate-based depot drug form for which the rate of release of the active substance in vitro can be adjusted very precisely is described.

5 Claims, No Drawings

ALGINATE-BASED VERAPAMIL-CONTAINING DEPOT DRUG FORM

DESCRIPTION

The present invention relates to the preparation of a verapamil-containing alginate-based depot drug form.

It has already been disclosed that alginates can be used for preparing depot drugs (Pharm. Ind., 33, 296 (1971) and Arzneim. Forsch. (Drug Res.) 25, 1272 (1975)). The alginate contained in the drug form swells in the gastric or intestinal fluid to form a gel matrix which envelopes the active substance. The active substance is released from the drug form over a period of about 6 to 10 hours by diffusion and breakdown of the gel matrix.

To date, it has been possible to influence the release of active substance in alginate-based depot forms only by considerable alterations in the amount of alginate used, by alteration of the preparation process and by changing the amount and nature of the other auxiliaries used.

Thus, on the one hand, the use of different amounts of alginate, and thus an altered active substance/auxiliary ratio, has always resulted in a specific and different release of active substance from the particular depot form.

If, on the other hand, it has been necessary to comply with a release of active substance required for medical and biopharmaceutical reasons and fixed within narrowly defined specifications, to date there have regularly been serious problems because it has usually been possible for the above influencing variables, whose exact effects can be understood and controlled only with difficulty, to be kept only incompletely constant on the industrial scale.

This has become evident, in particular, when very discriminating in vitro test methods have been used (eg. USP paddle test at 50 rpm) and has lead to unreliable manufacture and has possibly put the market supply at risk.

The following are the particular practical objectives:

1. For a predetermined size, shape and formula of the drug (e.g. good patient compliance in terms of the external form) it should be possible to alter the release of active substance deliberately with the aim of changing the profile of action.

2. Despite a high-dose content of active substance, the resulting drug form should be small, and it should be possible to adjust the release to any desired value.

3. For a given formula and external form, and a previously defined preparation process of a product, the release of active substance should be kept constant within narrow limits over a long time and from batch to batch.

The object of the invention is to provide a process for the preparation of a verapamil-containing depot drug form which meets the said objectives and which, in particular, makes it possible to obtain a depot drug form for which the rate of release of the active substance can be adjusted very precisely and repeatably from batch to batch, where the depot drug form has the following in vitro release characteristics: (a) virtually zero order release and (b) release of active substance in % of active substance, measured as verapamil acid addition salt, in the range from 60 to 100% within 8 hours.

This object is achieved by a process of the said type, which is characterised in that an alginate whose viscosity in a 1% strength aqueous solution at 20° C. is within a range of $x \pm 10$ mPa.s, where x is a value between 30 and 500, is employed.

According to a preferred embodiment of the invention, x represents a value between 60 and 120. According to another preferred embodiment of the invention, an oblong film-coated tablet is prepared as depot drug form.

The active substance verapamil is preferably in the form of an acid addition salt, especially as hydrochloride. The verapamil-HCl:alginate ratio in the depot drug form is expediently from 1:0.7 to 1:3 by weight.

It has thus been found that the above problems and aims can be solved in a straightforward manner by using alginates whose viscosity are within the narrow limits defined accurately above (ie. suited to the objective).

The invention thus relates to various verapamil-containing alginate-based depot forms in which a specific, therapeutically required rate of release of the active substance is achieved by use of constant (Problem case 1. and 3.) or different amounts of alginate (Problem case 2.).

The alginate processed in the formulae is characterised in that its viscosity in a 1% strength aqueous solution is within a range of $x \pm 10$ mPa.s at 20° C., in which x is a value between 30 and 500.

The viscosity of the alginate must be within a narrow range of $\leq 20$ mPa.s. The narrower the range of viscosity, the narrower also are the limits on the liberation properties of the drug form.

The claimed viscosity range relates to the measurement of the viscosity using a Hake viscosimeter (Rheomat ® model 30) or using a Brookfield viscosimeter (model DV2). If the viscosity is measured with other instruments, the viscosity range may shift. It should further be noted that in the preparation of the 1% strength aqueous alginate solution for the determination of the viscosity the 1% strength alginate content is calculated on the basis of dried alginate.

The preparation of alginates is known (cf. Ullmanns Encyklopädie der technischen Chemie, 4th Edition, Volume 19, pages 245 to 246 and literature cited therein; W. H. McNeely, D. J. Pettitt in Whistler: Industrial Gums, 2nd Edition, Academic Press, New York, page 49 et seq.).

The alginates which are preferably used are those in which the ratio of mannuronic to guluronic acid is between 7:3 and 3:7, preferably between 6:4 and 4:6. The latter can be obtained, for example, from the Laminaria hyperborea alga.

Examples of suitable alginates are ammonium alginate, calcium alginate, sodium alginate or mixtures of these alginates. Sodium alginate is preferred.

The higher the molecular weight (viscosity) of the alginate, the lower is the rate of release of the active substance assuming the amount of alginate in the formula is kept constant. The narrower the limits of the range of viscosity, the smaller the variation in the release values from batch to batch.

Application of the invention makes it possible, in particular, to prepare without difficulty verapamil-containing depot drugs which have an alginate basis and comply with a release of active substance within narrow limits which is required from the medical viewpoint. In particular, this achieves a high degree of reliability of manufacture, and a particularly economic mode of manufacture can be ensured by the avoidance of faulty batches.

EXAMPLE 1

Preparation of Alginates

A dry mixture of brown algae which consisted of equal parts of Laminaria spec., Ascofyllum nodosum, Macrocystis spec., Lesonia spec., Ecklonia spec. and Durvillea spec. was coarsely comminuted in a cutting machine to produce pieces up to 3 cm long. The material obtained in this way was washed 3×alternately with hot water and 0.02 N hydrochloric acid to remove acid-soluble constituents. 50 kg of wet mass obtained in this way were vigorously stirred with 2000 l of 0.02 N sodium hydroxide solution at room temperature for 4 h. After sedimentation, the supernatant liquid (crude alginate solution) was aspirated off. Calcium chloride was added to the liquid which had been separated off until the crude alginate was virtually completely precipitated. The precipitate was filtered off, and 1 N hydrochloric acid was added until the pH of the suspension was at pH 1 to 2. The remaining precipitate (=alginic acid) was separated off and washed with cold water until the calcium content of the precipitate was below 0.3% (based on dry matter). The still moist alginic acid was then neutralized by mixing with sodium carbonate to give a paste with evolution of heat. After the paste had cooled to room temperature it was dried in a rotating tube oven at a temperature of 70° C. and 4 revolutions per min for about 8 h. 9.9 kg of sodium alginate with a viscosity of about 180 mPa.s were obtained.

Products with the viscosity range from 30 to 500 mPa.s can be obtained by varying the temperature range during the drying in the rotating tube oven from 50° to 90° C.

The desired particle distribution (98%<50 μm) was achieved by milling. This process caused a slight reduction in viscosity. A required viscosity can be adjusted where appropriate by mixing sodium alginates of different viscosities. However, the alginates to be mixed must not differ in their viscosities by more than about 60 mPa.s.

EXAMPLE 2

Preparation of Drugs

Depot drugs (film-coated tablets) of the following compositions were prepared:

Formula variant 1 (220 mg of sodium alginate)

| Verapamil hydrochloride | 240 mg | |
| Sodium alginate | 220 mg | |
| Auxiliaries | 205 mg | |
| | 665 mg | total weight of the oblong film-coated tablet |

Subvariant 1.1 with sodium alginate of viscosity 204 mPa.s

Subvariant 1.2 with sodium alginate of viscosity 348 mPa.s

Subvariant 1.3 with sodium alginate of viscosity 501 mPa.s

Formula variant 2 (320 mg of sodium alginate)

| Verapamil hydrochloride | 240 mg | |
| Sodium alginate | 320 mg | |
| Auxiliaries | 190 mg | |
| | 750 mg | total weight of the oblong film-coated tablet |

Subvariant 2.1 with sodium alginate of viscosity 87 mPa.s

Subvariant 2.2 with sodium alginate of viscosity 143 mPa.s

Subvariant 2.3 with sodium alginate of viscosity 204 mPa.s

Formula variant 3 (400 mg of sodium alginate)

| Verapamil hydrochloride | 240 mg | |
| Sodium alginate | 400 mg | |
| Auxiliaries | 120 mg | |
| | 760 mg | total weight of the oblong film-coated tablet |

Subvariant 3.1 with sodium alginate of viscosity 30 mPa.s

Subvariant 3.2 with sodium alginate of viscosity 62 mPa.s

Subvariant 3.3 with sodium alginate of viscosity 87 mPa.s

The following substances were employed in the following ratio of amounts as auxiliaries for preparing the tablet composition (core):

| Microcrystalline cellulose: | 40 to 55% |
| Povidone ®: | 25 to 35% |
| Purified water: | 15 to 25% |
| Magnesium stearate: | 0.5 to 2% |

It is also possible to employ lactose, other sugars or starches in place of cellulose. It is likewise possible to use starch mucilage or gelatine solution as binder. It is likewise possible to use customary flowability agents and lubricants.

Since verapamil-HCl is a very bitter and anesthetic substance, the tablet cores were taste-sealed with a film coating. The employed coating had the following composition:

| Hydroxypropylmethylcellulose | 4.9 mg |
| Polyethylene glycol 400 | 1.3 mg |
| Polyethylene glycol 8000 | 0.8 mg |
| Talc | 8.4 mg |
| Titanium dioxide | 6.2 mg |
| Colors | 0.1 mg |
| Wax | 0.3 mg |

On determination of the release of active substance with simulated gastric and intestinal fluid (paddle test according to DAB 9 and USP XXI, 50 rpm, 900 ml, 37° C., test medium changed from pH 1.2 to 7.4 after the first hour [single change]) the following release of active substance was found:

The release of active substance was virtually linear (0 order release), i.e. pH independent, for all formula variants. The release of the active substance from the tablets after a test time of 8 hours was as follows:

| Variant | Release of active substance, × 6, CV < 5%<br>Verapamil-HCl in % |
|---------|------|
| 1.1 | 94 |
| 1.2 | 83 |
| 1.3 | 70 |
| 2.1 | 90 |
| 2.2 | 81 |
| 2.3 | 72 |
| 3.1 | 92 |
| 3.2 | 79 |
| 3.3 | 69 |

The release values found for the above formula variants showed that any required release of active substance can be achieved even when different amounts of alginate are used by specific choice of the alginate type suitable in each case. The application of this process makes it possible for the first time to prepare very reliably and with difficulty alginate-based verapamil depot drug forms.

We claim:

1. Process for the preparation of an alginate-based verapamil-containing depot drug form for which the rate of release of the active substance can be adjusted very precisely and repeatably from batch to batch, where the depot drug form has the following in vitro release characteristics: (a) virtually zero order release and (b) release of active substance in % of active substance, measured as verapamil acid addition salt, in the range from 60 to 100% within 8 hours, characterised in that an alginate whose viscosity in a 1% strength aqueous solution at 20° C. is within a range of $x \pm 10$ mPa.s, where x is a defined value, which is constant for all batches, between 30 and 500, is employed.

2. Process according to claim 1, characterised in that an alginate whose viscosity in a 1% strength aqueous solution at 20° C. is within a range of $x \pm 10$ mPa.s, where x has a defined value, which is constant for all batches, between 60 and 120, is employed.

3. Process according to claim 1 characterised in that the depot drug form is prepared as oblong film-coated tablet.

4. Process according to claim 2 characterised in that the depot drug form is prepared as oblong film-coated tablet.

5. Process according to any one of claims 1, 2, 3, or 4, characterised in that a verapamil-HCL:alginate ratio of from 1:0.7 to 1:3 by weight is present in the depot drug form.

* * * * *